United States Patent [19]

Litt et al.

[11] Patent Number: 5,026,837
[45] Date of Patent: Jun. 25, 1991

[54] DNA PROBE WHICH REVEALS A HYPERVARIABLE REGION ON HUMAN CHROMOSOME 16

[75] Inventors: Michael Litt, Portland, Oreg.; Linda L. Bufton, Palo Alto, Calif.

[73] Assignee: The State of Oregon acting by and through the State Board of Higher Education on behalf of Oregon Health Sciences University, Eugene, Oreg.

[21] Appl. No.: 103,021

[22] Filed: Sep. 30, 1987

Related U.S. Application Data

[63] Continuation-in-part of Ser. No. 46,831, May 4, 1987, and a continuation-in-part of Ser. No. 53,320, May 22, 1987, and a continuation-in-part of Ser. No. 54,760, May 27, 1987.

[51] Int. Cl.$^5$ .................... C07H 21/04; C12Q 1/68
[52] U.S. Cl. ................................. 536/27; 435/6; 435/172.3; 436/501; 935/78
[58] Field of Search .............. 435/6, 172.3; 436/501; 536/27; 935/78

[56] References Cited

U.S. PATENT DOCUMENTS

| | | |
|---|---|---|
| 4,302,204 | 11/1981 | Wahl et al. ........................ 23/230.3 |
| 4,358,535 | 11/1982 | Falkow et al. ......................... 435/5 |
| 4,399,216 | 8/1983 | Axel et al. ............................. 435/6 |
| 4,468,464 | 8/1984 | Cohen et al. ....................... 435/317 |
| 4,594,318 | 6/1986 | Gusella et al. ......................... 435/6 |
| 4,599,303 | 7/1986 | Yabusaki et al. ...................... 435/6 |
| 4,623,619 | 11/1986 | Owerbach et al. .................... 435/6 |

OTHER PUBLICATIONS

Jeffreys et al., "Individual-Specific 'Fingerprints' of Human DNA," Nature 316:76-79 (1985).
Wyman and White, "A Highly Polymorphic Locus in Human DNA," *Proc. Natl. Acad. Sci., U.S.A.,* 77:6754-6758 (1980).
Nakamura et al., "Characterization of a Human 'Midisatellite' Sequence," *Nucl. Acids Res.,* 15:2537-2547 (1987).
Buroker et al., "A Hypervariable DNA Region on Human Chromosome 1p," *Genetics,* 113: Supplement No. 1, Part 2, p. S64 (1986).
Litt et al., "A Highly Polymorphic Locus in Human DNA Revealed by Probes from Cosmid 1-5 Maps to Chromosome 2q35-37," *Am. J. Hum. Genet.,* 38:288-296 (1986).
Litt & White, "A Highly Polymorphic Locus in Human DNA Revealed by Cosmid-Derived Probes," *Proc. Natl. Acad. Sci. U.S.A.,* 82:6206-6210 (1985).
Bufton et al., "Four Restriction Fragment Length Polymorphisms Revealed by Probes from a Single Cosmid Map to Chromosome 19," *Am. J. Hum. Genet.,* 38:447-460 (1986).
Buroker et al., "A Hypervariable Region at the D19S11 Locus," *Hum. Genet.,* 76:90-95 (1987).
Bufton et al., "A Highly Polymorphic Locus on Chromosome 16q Revealed by a Probe from a Chromosome-Specific Cosmid Library," *Hum. Genet.,* 74:425-431 (1986).
White et al. (1986) in *DNA Probes, Applications in Genetic and Inf. Disease and Cancer* (Ed. L. S. Lerman, Cold Spring Harbor Labs., Cold Spring Harbor, N.Y.), pp. 43-47.
Darby et al. (1986), Nucleic Acids Research, vol. 14, No. 23, p. 9543.

*Primary Examiner*—Robert A. Wax
*Assistant Examiner*—Ardin H. Marschel
*Attorney, Agent, or Firm*—Klarquist, Sparkman, Campbell, Leigh & Whinston

[57] ABSTRACT

A DNA probe p79-2-23 is homologous to at least a portion of a hypervariable DNA region located on chromosome 16q22→q24 in the human genome. The DNA region displays a restriction fragment length polymorphism when digested with certain restriction endonucleases. Unrelated individuals display unique fragment patterns on Southern blots probed with p79-2-23. The probe can be used to produce a genetic "fingerprint" for establishing human identity, determining engraftment of bone marrow transplants, determining parentage, and otherwise mapping genes.

12 Claims, 9 Drawing Sheets

FIG. 1

0.3% AGAROSE GEL

FIG.4a  FILTER 33a PROBED WITH TOTAL HUMAN DNA

FIG.4b  FILTER 33b PROBED WITH TOTAL MOUSE DNA

FIG.5a — 0.45% AGAROSE GEL (COSMIDS FROM FREEZING MEDIUM)

FIG.5b — 0.4% AGAROSE GEL (PLATE 32 COSMIDS) — SAMPLE WELLS

DNA PROBE WHICH REVEALS A HYPERVARIABLE REGION ON HUMAN CHROMOSOME 16

This invention was made with government support under research which was funded in part by grant RO1GM 32500 from the National Institutes of Health. The government has rights in the invention.

CROSS REFERENCE TO RELATED APPLICATION

This is a continuation-in-part of copending U.S. patent applications Ser. No. 046,831, filed May 4, 1987, under attorney Docket No. 29864, and entitled "A DNA PROBE WHICH REVEALS A HYPERVARIABLE REGION ON HUMAN CHROMOSOME 1," Ser. No. 053,320, filed May 22, 1987, under Attorney Docket No. 29865, and entitled "A DNA PROBE WHICH REVEALS A HYPERVARIABLE REGION ON HUMAN CHROMOSOME " and Ser. No. 054,760, filed May 27, 1987, under Attorney Docket No. 29863, and entitled "A DNA PROBE WHICH REVEALS A HYPERVARIABLE REGION ON HUMAN CHROMOSOME 2."

BACKGROUND OF THE INVENTION

1. Field of the Invention

The present invention concerns a restriction enzyme mapping probe for human chromosome 16.

2. General Discussion of the Background Restriction fragment length polymorphisms (RFLPs), which are differences among individuals in the lengths of particular restriction fragments, are useful markers for mapping the human genome. Botstein, et al., *Am. J. Hum. Genet.*, 32:314–331 (1980). As the number of known RFLPs increases, they are becoming ever more useful in the prenatal or early diagnosis of numerous hereditary diseases. RFLPs are also used in mapping a diseased gene to a specific chromosomal location, which may serve as the first step in cloning the gene.

Diseases that have been mapped by linkage studies with RFLPs include Huntington's Disease, Gusella, et al., *Nature*, 306:234–238, (1983); Duchenne's muscular dystrophy, Murray, et al., *Nature*, 300:542–544, (1982); X-Linked Retinitis Pigmentosa, Bhattacharya, *Nature*, 309:253–255 (1984); adult polycystic kidney disease, Reeders, et al., *Nature*, 317:542–544 (1985); and cystic fibrosis, Tsui, et al., *Science*, 230:1054–1056 (1985). RFLPs also have been crucial to the elucidation of mechanisms underlying hereditary cancer syndromes frequently associated with chromosome deletions such as retinoblastoma, Cavenee, *Nature*, 305:779–784 (1983), and Wilm's tumor, Koufos, et al., *Nature*, 309:170–172 (1984). In the future, RFLPs may be useful in characterizing the genetic contributions to susceptibility to common diseases which tend to cluster in families, such as colon cancer and schizophrenia, White, et al., *Nature*, 313:101–105 (1985). For example, U.S. Pat. No. 4,623,619 discloses a method of using a probe to determine the liability of human individuals to develop atherosclerosis.

RFLPs can also provide individual-specific "fingerprints" of human DNA which can be used for such forensic purposes as identification of corpses, paternity testing, and identification of rapists. For example, Jeffreys, et al. disclosed in *Nature*, 316:76–79 (1985) that simple tandem-repetitive regions of DNA ("minisatellites") which are dispersed throughout the human genome frequently show substantial length polymorphism arising from unequal exchanges which alter the number of short tandem repeats in a minisatellite. The repeat elements in a subset of human minisatellites share a common 10–15 base-pair core sequence. A hybridization probe consisting of the core repeated in tandem can detect many highly polymorphic minisatellites simultaneously to provide a set of genetic markers of general use in human linkage analysis. Certain probes can detect sets of hypervariable minisatellites to produce somatically stable DNA "fingerprints" which are completely specific to an individual (or an identical twin) and can be applied directly to problems of human identification, including parenthood testing. Unfortunately, the Jeffreys, et al., probe detects repeated sequences that occur throughout the entire human genome, and gives rise to very complex electrophoresis patterns that are sometimes difficult to interpret.

Hypervariable DNA regions have been reported near the human insulin gene (Bell, et al., *Nature*, 295:31–35 (1982)), in the α-globin gene cluster (Higgs, et al., *Nucleic Acids Res.*, 9:4213–4224 (1981); Proudfoot, et al., *Cell*, 31:553–563 (1982); Goodbourn, et al., *Proc. Natl. Acad. Sci. U.S.A.*, 80:5022–5026 (1983)), near the c-Ha-Ras-1 oncogene (Capon, et al., *Nature*, 302:33–37 (1983)) and at the telomere of the X and Y chromosomes (Cook, et al., *Nature*, 317, 687–692 (1985)). In all cases where DNA sequence information in these regions is available, it shows that the region consists of tandemly repeated sequences which vary in copy number among chromosomes. These hypervariable regions are hypothesized to arise by mitotic or meiotic unequal crossing over or by DNA slippage during replication (Jeffreys, et al., 1985). Hypervariable regions give rise to highly polymorphic loci at numerous genomic sites. DNA probes from such regions have been useful in paternity testing and other forensic applications as well as in human gene mapping.

It is therefore a primary object of this invention to provide a DNA probe which detects a hypervariable region of a human chromosome.

Another primary object is to provide such a probe which is specific to a single human chromosome.

Yet another primary object is to provide a probe which is easy to use and gives consistent results in forensic and medical tests.

SUMMARY OF THE INVENTION

The present invention includes a DNA probe, which is substantially homologous to at least a portion of a hypervariable DNA region located on the distal half of the long arm of chromosome 16q22→q24 in the human genome. The DNA region displays a restriction fragment length polymorphism in humans when digested with certain restriction endonucleases.

In the disclosed embodiment, the probe is p79-2-23. When used to probe Southern blots of TaqI-digested DNA's from 51 unrelated Northern European Caucasians, p79-2-23 found eleven allelic fragments ranging in size from 3.0 to 7.3 kilobases (kb). The same locus was detected with several other enzymes, including EcoRI, MspI, RsaI, Pvu II, and Hind III.

A major advantage of p79-2-23 is that it has at least eleven allelic fragments and a polymorphism information content of 0.77. The probe is a 1450 bp segment of human chromosome 16 cloned into the BamHI site of the vector pSP65. Preferably, the probe is radioactively labelled with $^{32}$p and, in use, is hybridized with a Southern blot made from TaqI or RsaI digested human DNAs.

Broadly defined, the invention includes a recombinant DNA molecule containing a sequence substantially identical or homologous to at least a portion of the inserted sequence of probe p79-2-23, the sequence being flanked by DNA segments that are not substantially the same as the DNA that flanks the inserted sequence in human chromosome 16. The recombinant DNA molecule consists of segments of DNA from different genomes which have been joined end-to-end outside of living cells. The invention also includes a vector containing a heterologous DNA sequence which is substantially identical or homologous to at least a portion of p79-2-23.

The present invention includes a method of producing a genetic band pattern or "fingerprint" by digesting a human genome with a restriction endonuclease which produces allelic fragments when probed with p79-2-23. The fragments are then separated by agarose gel electrophoresis, partially transferred to a nitrocellulose filter, and exposed to radioactively labeled p79-2-23. The labeled probe hybridizes to fragments of DNA on the filter having homologous sequences. Autoradiographs produce a distinct band pattern which is used in human gene linkage analysis.

Probe p79-2-23 produces distinct band patterns which are characteristic of the individual from which the genome was taken. The band pattern can therefore be used for such forensic purposes as establishing the identity of a disfigured corpse or an accused assailant in a rape case. Medical applications include determining engraftment of bone marrow transplants, where it is helpful to determine if the marrow propagating in a patient's bone is diseased original tissue or healthy graft tissue. The probe can also be used to determine parentage because band patterns produced by the probes are inherited in a simple Mendelian fashion. Probe p79-2-23 is also useful in mapping genes because the probe marks a specific region on the distal half of the long arm of human chromosome 16 and can monitor loss of chromosome 16 during tumorigenesis.

A major advantage of p79-2-23 over more highly polymorphic probes previously described is that the allelic fragments which it detects cover a broder size range and are therefore easier to resolve by agarose gel electrophoresis. The probe is therefore easy to use and gives consistent results.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 6 shows deleted cosmids.

FIG. 7 is an autoradiograph showing the initial screening of cosmid CF33-79.

FIG. 9 is an autoradiograph of an RsaI blot of 18 unrelated individuals probed with oligo labeled p79-2-23.

FIG. 10a is a Southern blot of RsaI digested DNA from 15 individuals of family K1331, the blot having been probed with p79-2-23, a family tree schematically illustrating the relationship of the individuals from whom the probed DNA was obtained.

FIG. 10b is a Southern blot of TaqI digested DNA from 12 individuals of family K1340, the blot having been probed with p79-2-23, a family tree schematically illustrating the relationship of the individuals from whom the probed DNA was obtained.

FIG. 11 is a photograph of a Southern blot of Hind III digests of DNAs from parental and hybrid cell lines probed with p79-2-23.

FIG. 12a is a photomicrograph of in situ hybridization of cosmid CF33-79 showing a representative metaphase that has been R-banded following hybridization.

FIG. 12b is a photomicrograph of the in situ hybridization shown in FIG. 12a after it has been destained and restained with Wright's stain to show silver grains.

FIG. 13 is a histogram of chromosomal distribution of silver grains from in situ hybridization of cosmid CF33-79 to chromosomes of a normal male.

DETAILED DESCRIPTION OF PREFERRED EMBODIMENT

For the construction of linkage maps of human chromosomes, marker loci with multiple alleles and a polymorphism information content (PIC) near one are very useful. Botstein, et al., *Am. J. Human Genet.*, 32:314–331 (1980). Although several hundred RFLPs have been reported to date, only about 10 percent have PIC values >0.5. Willard, et al., *Cytogenet. Cell Genet.*, 40:360–490 (1985). The present inventors have addressed this problem of RFLP's having low PICs by using a method for rapidly screening cosmids and other repeat-containing DNA clones to identify those with inserts homologous to genomic regions especially rich in RFLPs. Litt and White, *Proc. Nat'l. Acad. Sci. USA*, 82:6206–6210 (1985).

Probe p79-2-23 was isolated by constructing a partial genomic DNA library using cosmid vectors and DNA from a somatic cell hybrid. A complete DNA library was not used because random RFLPs on only chromosome 16 were being sought.

The library, once constructed, was screened with total human and total mouse DNA probes to select those containing inserts which represented about 2.5 percent of the total clones. Clones with human inserts were screened for those identifying RFLPs, and the latter were further screened to isolate single copy probes useful for specific, highly polymorphic RFLPs. Gusella et al., *Proc. Natl. Acad. Sci. USA*, 77:2829–2833 (1980) has shown that repetitive sequences in mammals have diverged sufficiently between species such that total human and total rodent DNAs could be used as species-specific probes by using hybridization conditions under which only repetitive sequences would give a detectable hybridization signal.

Chromosomal location was verified using a rodent-human hybrid mapping panel with more precise localization done by in situ hybridization.

A. Materials and Methods

1. Construction of the 11q and 16q DNA Library in Cosmids a. Somatic Cell Hybrid DNA Preparation The somatic cell hybrid, CF 52-46-⅓, containing the translocated human chromosome 11 q/16q, was from T. Mohandas, Harbor-UCLA Medical Center, Los Angeles, Calif. The cells, received as frozen pellets, were diploid mouse cells containing as the only human DNA at least one translocated 11q/16q with about 15 percent of cells containing two or more copies of this chromosome. As 11q+16q represent about 5 percent of the haploid genome (Daniel, *Clin. Genet* 28:216-224, 1985), this translocated chromosome should represent at least 2.5 percent of the somatic cell hybrid DNA.

High molecular weight DNA (>200 kb) was isolated from the cells using procedures combined from Maniatis et al., *Molecular Cloning, A Laboratory Manual*, (New York, Cold Spring Harbor Laboratory, 1982) and (Bell et al, *Proc. Nat'l Acad.-Sci. USA* 78:5759-5763, 1981). About $1.2 \times 10^8$ cells were received frozen in 2.5 ml of 10 mM Tris Cl$^-$, 150 mM NaCl, 10 mM EDTA, and 10 percent glycerol. They were thawed and pelleted at 2 Krpm at 4 degrees C. for 5 minutes and the supernatant discarded. The cells were resuspended in 50 ml of BCL buffer, centrifuged at 2 Krpm at 4 degrees C. for 20 minutes, the supernatant discarded and the pellet drained briefly. The pellet was gently resuspended in 12 ml ice cold NL buffer on ice. To another 12 ml of NL buffer was added 2.5 mg Proteinase K (Boehringer Mannheim) and 1.2 ml 10 percent SDS. While gently vortexing this second solution, the nuclear suspension was added to it dropwise. The nuclear lysate was incubated overnight at 37 degrees C. with gentle rotation.

The sample was then extracted twice with an equal volume of phenol/chloroform (1:1), and once with chloroform for 30 minutes with gentle rolling on a rotating platform, centrifuged at 28 Krpm for 10 minutes and the top layer removed to a new tube. After dialysis overnight at 4 degrees C. against 4 L of dialysis solution A, the sample was transferred to a 50 ml tube and treated for 2 hours at 37 degrees C. with 100 μg/ml RNAse. 100 μg/ml Proteinase K and 0.5 percent SDS were added and the sample was incubated another hour at 37 degrees C. The sample was extracted twice with phenol/chloroform and once with chloroform using gentle rotation, dialyzed overnight at 4 degrees C. against 4 L of TE, loaded dropwise onto at least 2 volumes of 1M NaCl in TE in 38 ml polyallomer tubes and centrifuged overnight in a Beckman SW27 rotor at 25 Krpm. The supernatant was poured off and the tubes drained 10 minutes. The pellets were dissolved in a small volume of TE overnight at 4 degrees C. with gentle shaking. The yield, checked by UV spectrophotometry, was about 500 μg per $10^8$ cells (assuming that 1 mg/ml of DNA has an $A_{260}=20$ in a 1 cm cuvette). The size was estimated at about 200 kb by electrophoresis in a 0.3 percent agarose gel using uncut λ DNA for comparison.

The high molecular weight DNA was partially digested with one unit of Sau 3A per 128 μg DNA using the conditions determined by a series of test digests to give a maximum number of fragments in the 35-45 kb size range (Maniatis et al., 1982). The enzyme was heat inactivated by incubating the digest at 68 degrees C. for 10 minutes, and the DNA was ethanol precipitated and dissolved in TE. The partial digest was then size fractionated using a 10-30 percent sucrose density gradient with 10 percent and 30 percent sucrose solutions made in 1M NaCl, 20 mM Tris Cl$^-$, and 5 mM EDTA (Maniatis et al., 1982). Samples were layered onto the gradient in Beckman 12.8 ml ultra-clear centrifuge tubes and were centrifuged in a Beckman SW41 rotor at 23 Krpm for 14 hours at 20 degrees C. Fractions were collected using a rigid plastic tube connected to flexible tubing which was connected to a Gilson minipuls pump. The plastic tube was placed vertically into the sample tube so that it was almost touching the bottom, and 0.75 ml fractions were collected using this pump set-up with a Gilson fraction collector. Aliquots were analyzed on a 0.4 percent agarose gel and those containing DNA in the 35-45 kb size range were pooled, ethanol precipitated, and the pellets dissolved in TE.

b. Vector DNA

Figure 1:
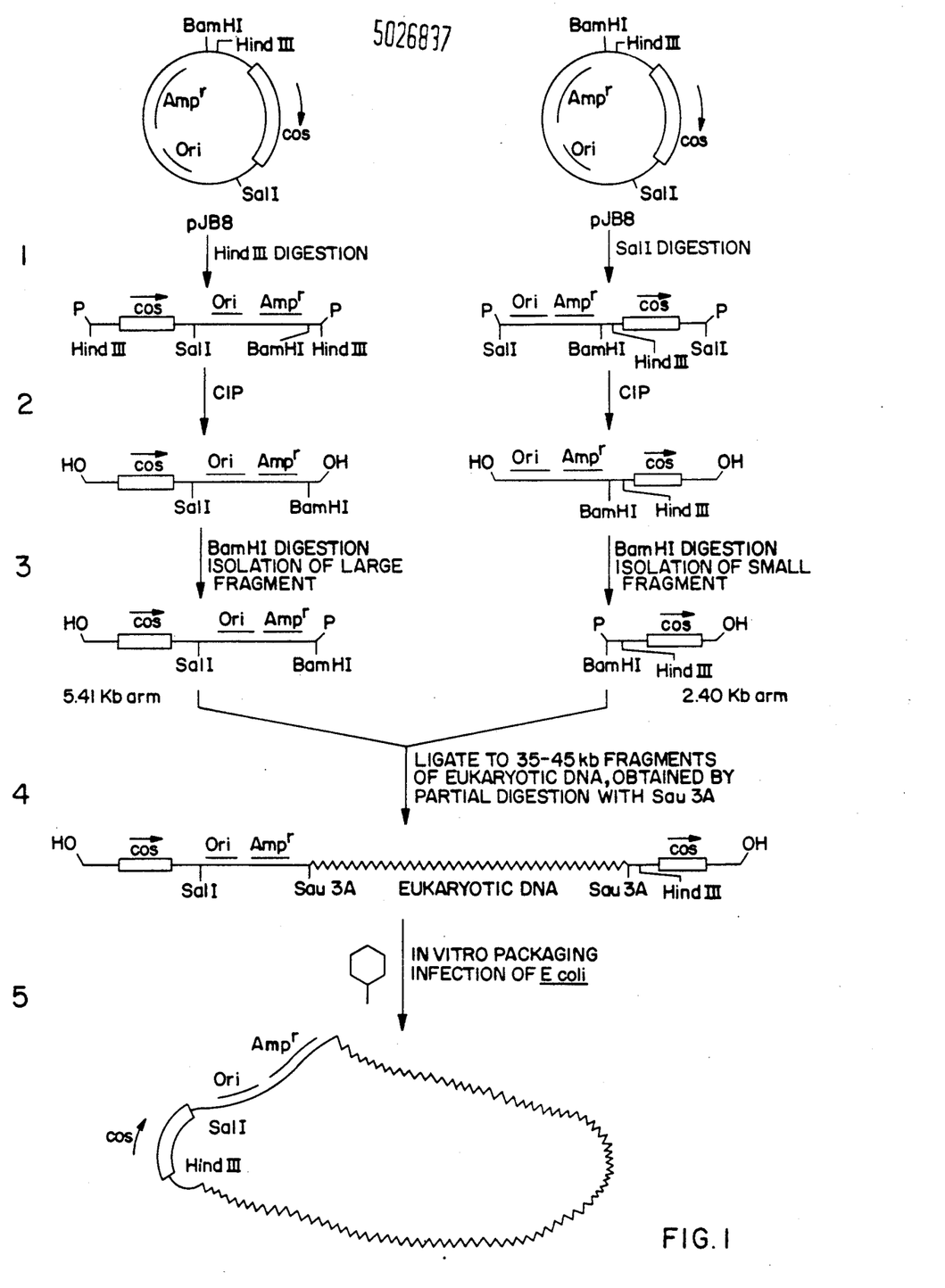
FIG. 1 shows the cloning scheme for preparing the cosmid library of the present invention.

The cosmid vector pJB8, shown in FIG. 1, was used for this library. Prepared pJB8 arms with end BamHI sites (steps 1-3, FIG. 1) were obtained from Amersham Corporation, Arlington Heights, Ill.

c. Ligation, in vitro Packaging, and Transduction Into Host Bacteria

The general scheme used is shown in FIG. 1 (modified from Maniatis et al., 1982). Ligations were done at a total DNA concentration of 165 μg/ml with the molar ratio of vector molecules to insert at 1:1:1 as the desired concatamer was vector arm 1 (HindIII/BamHI): insert: vector arm 2 (BamHI/SalI)(Maniatis et al., 1982). The DNA was ligated overnight at 15 degrees C. in 50 mM Tris Cl$^-$, pH7.4, 10 mM MgCl$_2$, 1 mM spermidine, 5mM dithiothreitol, 1 mM ATP, and 100 μg/ml bovine serum albumin with 1 unit of Boehringer Mannheim T$_4$ DNA ligase per 20 μl reaction for 3 μg of DNA. Ligation was monitored on a 0.3 percent agarose gel by disappearance of unligated vector arms and increased size of the smear of insert DNA due to concatamerization.

As shown in FIG. 1, after ligation an entire complement of plasmid sequence is contained between the 2 cos sites. Concatamers are efficiently packaged if the cos sites, the substrates for a packaging depending cleavage, are 37-52 kb apart or 75-105 percent the size of λ DNA. Old and Primrose, *Principles of Gene Manipulation*, 3rd ed. (Oxford, Blackwell Scientific Publications 1985). Following in vitro packaging and introduction into *E. coli*, the cosmid DNA recircularizes and replicates in the form of a large plasmid which contains the β-lactamase gene that confers ampicillin resistance on the host bacteria (Maniatis et al., 1982).

The ligated DNA was packaged into bacteriophage λ particles in vitro using the "Packagene" extract system from Promega Biotec according to the manufacturer's instructions, with 0.5 μg of DNA and ½ tube of extract per reaction. The packaged DNA was transduced into 3 different *E. coli* host strains: HB101, ED8767, and DK-1. For use in transduction, the bacteria were grown up overnight in L broth with 0.4 percent maltose, pelleted, and resuspended in 0.5 volume of 10 mM MgSO$_4$ or 10 mM MgCl$_2$. Fifty microliters of packaging reaction was mixed with 100 μl SM and 200 μl of host bacteria. The λ particles were allowed to adsorb at 37 degrees C. for 20 minutes, then 1 ml of L broth was added and the mixture was incubated at 37 degrees C.

for 45 minutes to allow expression of ampicillin resistance. The cells were pelleted, resuspended in 200 μl of L broth and spread on day old L agar+200 μg/ml ampicillin plates. Plates were inverted and incubated overnight at 37 degrees C.

Two methods were used for storing parts of the library. The first method was toothpicking transformed colonies from the original plates into 150 μl of freezing medium with 200 μ/ml ampicillin in 96-well tissue culture plates which were kept at −70 degrees C. (Schleif and Wensink, *Practical Methods in Molecular Biology*, New York, Springer-Verlag, 1981). The second method was to toothpick transformed colonies from the original plates onto 150×15 mm L agar+200 μg/ml ampicillin plates using a grid template for 520 colonies per plate. Plates were wrapped and stored at 4 degrees C.

2. Screening the Cosmid Library a. Preparation of replica filters

Replica filters were made from the master plates and processed using procedures modified from Grunstein and Hogness, *Proc. Nat. Acad. Sci. USA*, 72:3961–3965, (1975). Colonies were transferred from the 96-well plates to sterile nitrocellulose filters (Millipore HATF or Schleicher and Schuell BA 85) on L-agar+200 μg/ml ampicillin plates using a stainless steel 96-pin replicator (West Coast Scientific). Replica filters were made from the master grid plates by placing a sterile filter on the surface of the toothpicked plate, notching the filter with an 18 gauge needle at asymmetric points also marked on the master plate, then transferring the filter, colony side up, to a fresh L-agar+ampicillin plate. In both cases, the filters were incubated at 37 degrees C. until colonies were visible.

Replica filters were prepared for colony hybridization as follows: they were placed, colony side up for 5 minutes each, on a series of 3 3 MM Whatman filter papers moistened with 10 percent SDS, 0.5M NaOH/1.5M NaCl, and 1.5M NaCl/0.5M Tris Cl−, pH 7.5, respectively, with brief blotting on paper towels between steps. They were then wetted with 1X SET, dipped through a 100 μg/ml solution of Proteinase K in SET and placed on SET-moistened 3 MM sheets to incubate for 30 minutes at room temperature. They were then dipped through a solution of SET, dried on paper towels, sandwiched individually between 3 MM sheets, and baked in a vacuum oven at 60–80 degrees C. for 1–2 hours. The filters were then washed at 45 degrees C. in prewash solution for 1–2 hours. Finally, they were prehybridized in SEAL-A-MEAL bags overnight at 45 degrees C. in prehybridization/hybridization solution (without dextran sulfate).

F filters, stored at −70 degrees C. as back ups, were made and incubated on L-agar+ampicillin plates containing 5 percent glycerol. They were prepared for freezing by placing them on sterile 3 MM filter paper, placing a second freshly wetted filter on top, sandwiching the two filters together between more 3 MM sheets by pressing with a heavy weight, and placing the sandwich with a moistened sheet in a SEAL-A-MEAL bag (Hanahan and Meselson, Gene, 10:63–67, 1980).

At one point, three of the F filters were thawed, several cosmid-containing HB 101 clones toothpicked from each filter into L-Broth, and fresh overnight cultures grown up. Intact cosmid DNA purified from these overnight cultures was then packaged in vitro and transduced into DK-1.

b. Colony screening

To determine which clones contained human DNA inserts, one set of replica filters was probed with radioactively labeled total mouse DNA and a duplicate set with total human DNA. Total mouse DNA was prepared from mouse fibroblast line GM 346-A9 provided by T. Mohandas using the high molecular DNA preparative method previously described. Total human DNA from a random individual was prepared from white blood cells as described in section 3a. The mouse and human DNAs were labeled using the "oligo" or "primer extension" method of Feinberg and Vogelstein, Analyt. Biochem., 132:6–13 (1983) referred to subsequently as oligolabeling. The DNA was denatured at 100 degrees C. for 5 minutes, then incubated with a mixture of hexanucleotide primers and deoxynucleoside triphosphates (dNTPs), including $\alpha$-$^{32}$P deoxycytidine triphosphate (dCTP) or $\alpha$-$^{32}$P deoxyadenosine triphosphate (dATP). Radioactive $\alpha$-$^{32}$P dCTP and dATP with a specific activity of 10 millicuries(mCi)/ml were obtained from New England Nuclear.

A typical reaction was done in 25 μl consisting of 10 μl OLB, 2 μl 1 percent gelatin, 5 μl $\alpha$-$^{32}$P dATP (50 μCi), 2 units Klenow Polymerase I (Boehringer-Mannheim or Pharmacia), and 8 μl DNA (64 ng). Incubation was at room temperature for at least 2.5 hours, usually overnight. The percent incorporation was determined by spotting 0.1–0.5 μl of the reaction mix on Whatman GF/C glass fiber filter paper and scintillation counting before and after washing the filters with 5 percent trichloroacetic acid/0.1 percent sodium pyrophosphate. Specific activities ranged from $3 \times 10^8$ to $1 \times 10^9$ dpm/μg DNA.

The colony filters were hybridized in 1 ml of hybridization solution (same as prehybridization solution) per filter with $4 \times 10^6$ dpm/ml of radioactive total mouse or total human DNA in SEAL-A-MEAL bags overnight at 44–45 degrees C. The filters were washed once in 2X SSC/0.1 percent SDS at room temperature for 15 minutes, twice in 2X SSC/0.1 percent SDS at 55 degrees C. for 30 minutes and once in 1X SSC/0.1 percent SDS at 55 degrees C. for 30 minutes. They were dried on paper towels, wrapped in Saran wrap, taped to cardboard backing containing $^{14}$C India ink orientation marks, and exposed overnight to Kodak XAR-5 film backed by a Dupont Cronex Lightning-Plus Intensifier at −70 degrees C.

c. Preparation of DNA from cosmids containing human inserts

The rapid alkaline extraction method of Birnboim, *Methods in Enzymology*, 100:243–249 (1983) was used with some modifications. A fresh 5 ml overnight culture of the clone of interest was grown in L-broth+200 μg/ml ampicillin by inoculation from the master plate. One and a half milliliters of the culture was pelleted in an Eppendorf tube by a 15 second centrifugation, the supernatant discarded, and the pellet loosened by vortexing. The pellet was suspended in 200 μl lysozyme solution with 1 mg/ml fresh lysozyme (Sigma) and iced for 5 minutes. 400 μl alkaline SDS was added, the solution mixed gently by inversion 3–4 times, iced 5 minutes, 300 μl high salt solution added, the solution again mixed gently by inversion and iced 15 minutes, and the solution centrifuged at room temperature for 2 minutes. 700 μl of the supernatant was transferred to 2 fresh tubes and the DNA precipitated with 2.5 volumes of ethanol, pelleted and dissolved in acetate-MOPS, reprecipitated and again dissolved in acetate-MOPS, reprecipitated and dissolved in 80 μl TE$^{-4}$. DNA size and quantity were estimated by electrophoresis in a 0.4 percent agarose gel with known cosmids as size standards.

Larger scale cosmid DNA preparations were also attempted using similar alkaline lysis followed by centrifugation in cesium chloride-ethidium bromide density gradients (Maniatis et al., 1982).

d. Cosmid subcloning

Cosmids revealing possible polymorphisms were subcloned into the plasmid pSP65 (Promega Biotec), a 3 kb ampicillin resistant plasmid with a polylinker containing 11 unique restriction sites for cloning. Cosmid DNA was digested with 10X Sau 3A, phenol/chloroform extracted, ethanol precipitated, dissolved in TE$^{-4}$, and ligated into the BamHI site of BamHI cut and phosphatased pSP65 using 100 ng of insert DNA per 1 μg of vector DNA with reagents and conditions as previously described. Competent *E. coli* HB101 bacteria were transformed with the recombinant plasmids using standard techniques (Maniatis et al., 1982) and transformed colonies selected on ampicillin plates. Master plates and replica filters were made as previously described for cosmids except that 85 mm diameter filters were used with 100 colonies per filter. The clones were screened by colony hybridization using oligo-labeled total human DNA and appropriate oligolabeled restriction fragments from the cosmid. DNA was isolated from the subclones of interest by the Birnboim alkaline miniprep method (Birnboim, 1983).

3. Southern Blotting and Hybridization a. Source and preparation of human DNA

Human DNAs were prepared from outdated whole human blood obtained from the local blood bank and from lymphoblast cell lines of large Utah families obtained from the Human Genetic Mutant Cell Repository, Institute for Medical Research, Camden, N.J., using the method of Kunkel (Bell et al., 1981) with the addition of a second ethanol precipitation in the presence of 2.5M ammonium acetate. Restriction enzymes were obtained from Promega Biotec, New England Biolabs, Bethesda Research Labs, and Boehringer Mannheim and used according to the manufacturers' instructions. Human DNAs were digested with 5-10 units of enzyme per microgram of DNA and completeness of digestion assessed by agarose gel electrophoresis of parallel digests containing λ DNA in addition to human DNA (Barker et al., Cell, 36:131-138 1984a). Complete digests were ethanol precipitated and dissolved in TE.

b. Southern blotting

The digested total human DNAs were electrophoresed through agarose gels, transferred to nylon membranes (Gene Screen from NEN, Genatran from D and L Filter, Woburn, Mass., or Zetapore from AMF-CUNO, Meriden, Conn.), washed and prehybridized according to Barker et al., *Am. J. Hum. Genet.*, 36:1159-1171 (1984b).

c. Hybridization

Radiolabeled whole cosmids were screened on the Southern blots for their utility in revealing RFLPs. They were nick translated (Barker et al., 1984a) in the presence of α-$^{32}$P dATP to give specific activities of at least $2 \times 10^8$ dpm/μg. After removal of unincorporated radioactivity by spermine precipitation (Hoopes and McClure, *Nucleic Acids Res.*, 9:5493-5504 1981), the cosmid probes were mixed with a vast excess (625 μg/100-200 ng cosmid DNA) of non-radioactive 2.5 mg/ml sonicated (500 bp) human placental DNA (Calbiochem), heated at 100 degrees C. for 10 minutes, and prehybridized to a c$_o$t of about 100 moles-sec/L by incubation in 0.12M Sodium phosphate, pH 7, at 65 degrees C. for 4-6 hours (Litt and White, Proc. Nat'l Acadm. Sci. USA, 82:6206-6210 1985).

These prehybridized probes were then hybridized with Southern blots of Taq I and Msp I digested genomic DNAs from a panel of unrelated individuals. One lane containing the somatic cell hybrid line CF 52-46-1/8 DNA was also included on later blots to detect cosmids containing mouse DNA that were missed in the first screening. Hybridization was overnight at 43-45 degrees C. in hybridization solution with dextran sulfate. The blots were then washed in 2X SSC/0.1 percent SDS at room temperature for 15 minutes, once in 0.1X SSC/0.1 percent SDS at room temperature for 15 minutes, and twice in 0.1X SSC/0.1 percent SDS at 65-69 degrees C. for 30 minutes. The blots were dried on paper towels, wrapped in Saran wrap, and exposed for 1 to 7 days to Kodak XAR-5 film backed by an intensifying screen at −70 degrees C.

Restriction fragments of the cosmid were also labeled and used as probes on Southern blots. They were cut out from low-melting-point (LMT) agarose gels, mixed with water at 2 ml per gram of gel, heated at 100 degrees C. for 10 minutes, and oligolabeled as previously described without further purification. Plasmid subclones were also oligolabeled and used as probes on Southern blots.

4. Somatic Cell Hybrid Mapping Panel

The mapping panel consisted of 23 cell lines provided by Children's Hospital, Boston. The G35 cell lines are human-hamster hybrids derived from fusion of the Chinese hamster cell line E-36 with white blood cells from a female carrier of the X/19W translocation t(X;19)(q23-25::q13)(Latt et al., *Chromosoma*, 57:135-153 1976). The G17 and G24 cell lines are human-mouse hybrids derived from fusion of the mouse cell line RAG with white blood cells of the X/19W translocation carrier (G17 lines) or the X/19B translocation t(X;19)(q1p13)(Brook et al., *Hum. Genet.* 68:282-285, 1984). The G89E5 and G95A4 cell lines were derived from fusions of white blood cells from a karyotypically normal male with the Chinese hamster cell lines YH21 and Wg3h, respectively. G35A5AzA and G35A5AzF are subclones of G35A5 selected in 8-azaguanine for loss of the der 19 translocation chromosome. These hybrid cell lines were characterized by both isozyme and cytogenetic techniques (Bruns et al., *Cytogenet. Cell Genet.*, 22:172-176, 1978; Bruns et al., *Biochem. Genet.*, 17:1031-1059, 1979). In addition, DNAs from these hybrids have also been analysed with cloned DNA probes for all chromosomes except the Y.

5. In Situ Hybridization

Probes p79-2-23, CF 33-79, and p391-2-42 were nick-translated according to the method of Harper and Saunders, (Chromosoma, 83:431-439, 1981) to a specific activity of $4 \times 10^7$ dpm/μg using [$^3$H]TTP (65 Ci/mmol) and [$^3$H]dCTP (60 Ci/mmol)(Amersham). p79-2-23 and CF33-79 were then prehybridized with total human DNA as previously described. In situ hybridization to metaphase spreads from normal male cells was performed according to Harper and Saunders (1981).

6. Terminology for Cosmids and Plasmids

Cosmids were named beginning with CF, to designate the somatic cell hybrid line, followed by the plate number and the clone number on that plate. For example, a clone from the second well in row C of 96-well plate 9 was called CF9C2. A cosmid from master gridded plate 33 at square 79 was called CF33-79.

The plasmids were designated by a small p followed by the cosmid square number, the subclone master plate number, and the square number of the subclone plate. For example, p79-2-23 was a subclone of cosmid CF33-79 from the 23rd square of subclone master plate 2.

B. Results

1. High Molecular Weight DNA

Figure 2:
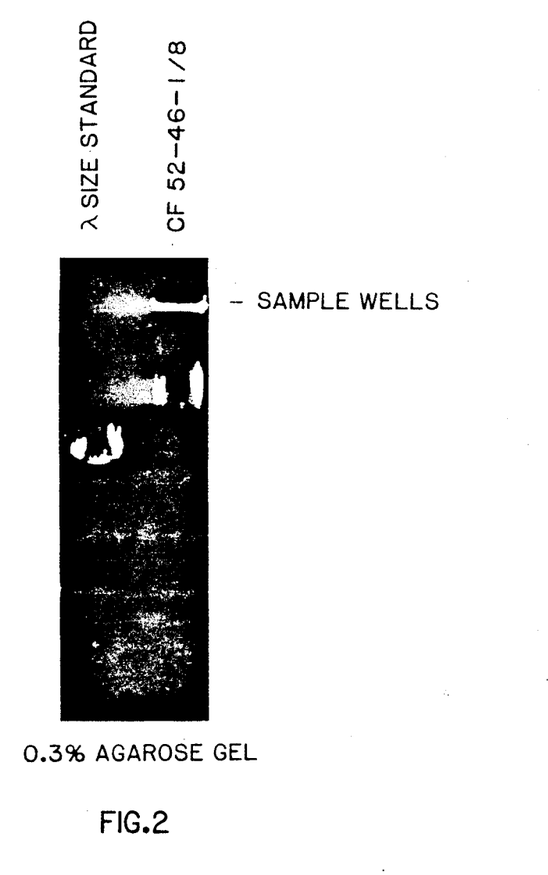
FIG. 2 shows a 0.3 percent agarose gel containing uncut bacteriophage γ DNA and CF52-46-1/8 DNA from a high molecular weight preparation.

FIG. 2 shows a 0.3 percent agarose gel containing uncut bacteriophage λ DNA and CF52-46-1/8 DNA from a high molecular weight preparation. The size of such large DNA cannot be accurately measured, but as very high molecular weight DNA does not separate well, DNA migrating well above the 50 kb λ DNA, as in this case, is likely greater than 200 kb in size (Maniatis et al., 1982).

After sucrose gradient size fractionation, 15 fractions were collected, and aliquots from every third fraction were checked for size on a 0.4 percent agarose gel. Fractions 5 through 8 contained DNA in the 35 to 45 kb size range and were pooled for use as insert DNA in subsequent ligations.

2. Ligation, In Vitro Packaging, and Transduction Into Bacterial Hosts

Figure 3A:
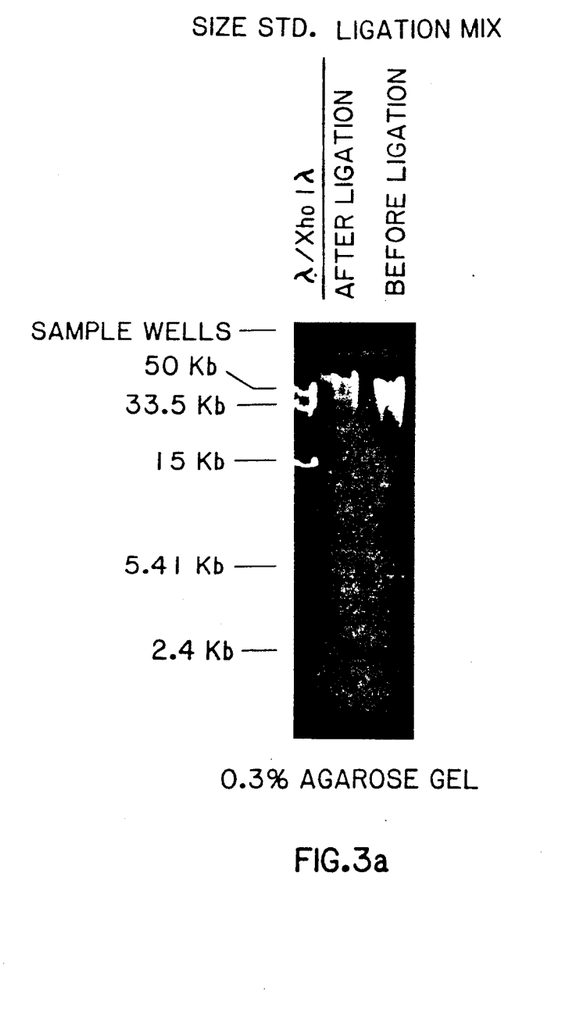
FIG. 3 shows two ligation test gels.
Figure 3B:
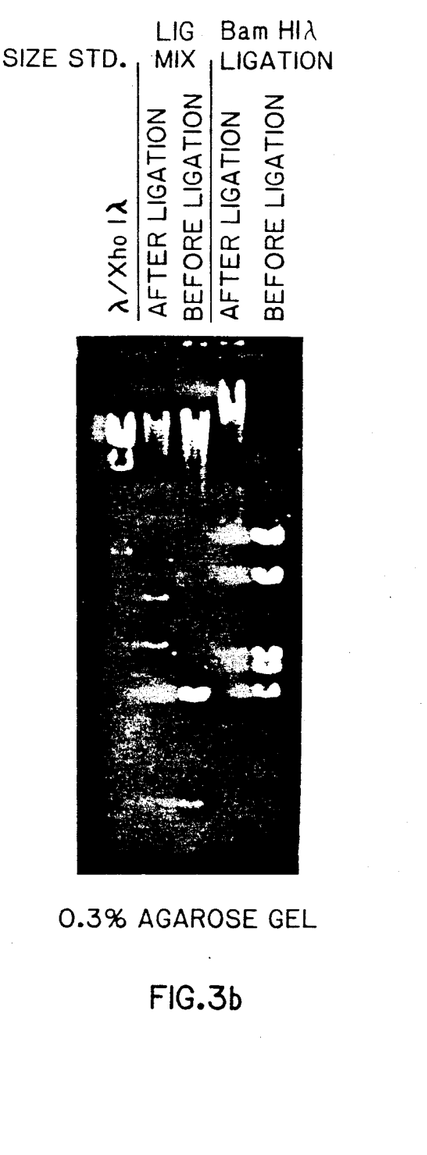

FIG. 3 shows two ligation test gels. Ligation is indicated by an increase in the size of the insert DNA smear due to concatamerization, by the partial disappearance of the 5.4 kb and 2.4 kb vector arms, and by the appearance of vector-vector ligation products of 10.8 kb (2 left arms), 7.8 kb (left arm + right arm), and 4.8 kb (2 right arms).

The efficiency of ligation was not measured. It could not be determined by gel monitoring of the appearance of high molecular weight DNA as the insert DNA was already very large. In fact, King and Blakesley, Focus, 8:1-3 (1986) found that efficiency does not correlate with the appearance of a very high molecular weight DNA. It could not be determined using transduction of E. coli as the DNA was first packaged in vitro adding another variable that influenced the efficiency of transduction. While the insert DNA shown in FIG. 3b did not increase as noticeably in size as the DNA in FIG. 3a, both gave similar numbers of transformants after packaging and transduction. As a complete library was not being constructed, maximum efficiency of ligation and packaging was not critical.

Initial transductions of the packaged ligation mix were done with E. coli strain ED8767. Efficiencies ranged from 3000 to 8000 colonies per microgram (µg) of total DNA. A total of about 2000 colonies from these transductions were transferred to either 96-well plates in freezing medium or to a gridded agar plate for storage and preparation of replica filters.

Later transductions were done using E. coli strain HB 101 with efficiencies of 3300 to 9000 colonies per µg of total DNA. These colonies were larger and appeared to grow better than those of ED8767. A total of about 1500 colonies were transferred to gridded agar plates for storage and preparation of replica filters.

One transduction was done with E. coli strain DK-1. The colonies were extremely small, efficiency was poor (800 colonies/µg total DNA), and the viability was poorer than for the other strains.

3. Screening the Library for Clones with Human Inserts

Figure 4A:
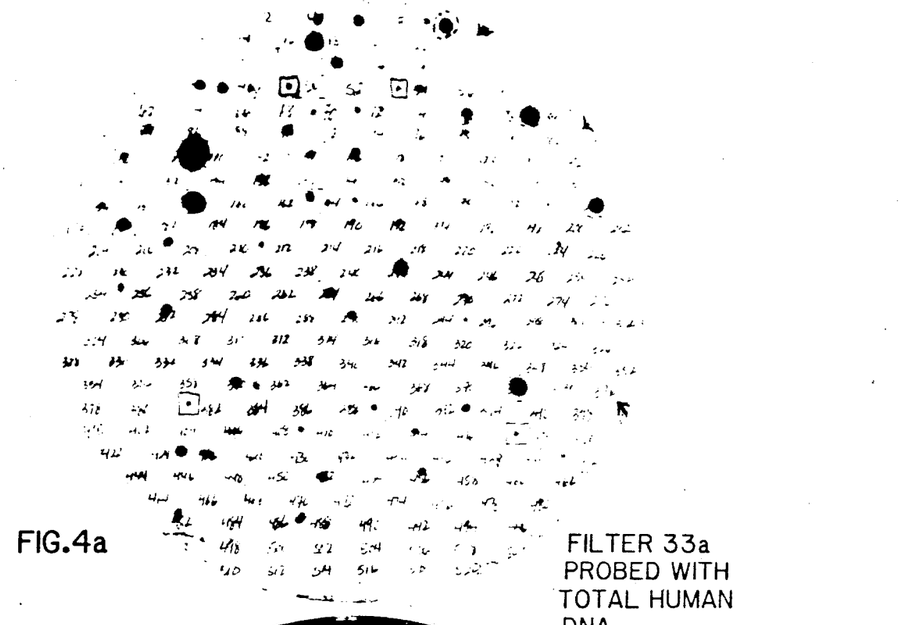
FIG. 4a shows an autoradiograph from the screening of a replica filter plate which was probed with total human DNA.
Figure 4B:
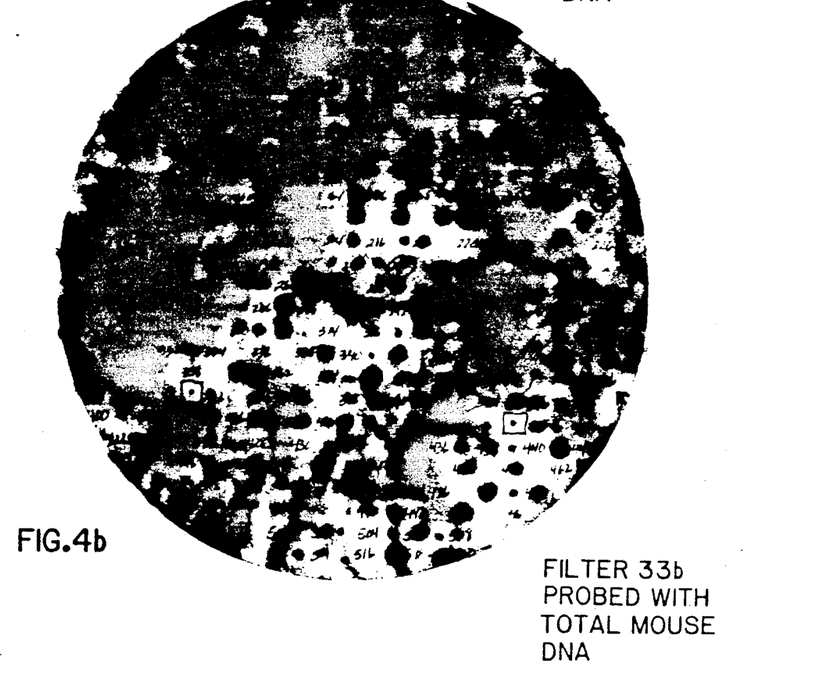
FIG. 4b shows an autoradiograph of a replica filter plate which was probed with total mouse DNA.

The cosmid screening results are shown in Table 1. From 3400 clones, one would expect at least 65 clones, or 2.5 percent, to contain human inserts based on the chromosome composition of the somatic cell hybrid line used to make the library. On screening of replica filters with total mouse and total human DNA, however, only 50 of 3400 clones, or 1.5 percent, appeared positive for human DNA and negative for mouse DNA. FIGS. 4a and 4b show two autoradiographs from the screening of plate 33. Filter 33a in FIG. 4a was probed with total human DNA; filter 33b in FIG. 4b with total mouse DNA. (Screenings were actually done in duplicate, i.e., two filters were probed with total human and two with total mouse.) Only 6 clones that light up with the total human probe, 79, 157, 176, 242, 372, and 393, light up faintly or not at all with the total mouse probe. A number of clones hybridized with both mouse and human probes.

TABLE 1

| Cosmid Screening Results | |
|---|---|
| Total colonies screened with total human and total mouse DNA | 3400 |
| Clones initially positive for human inserts | 50 |
| Cosmids with successful DNA preparations | 43 |
| Cosmids with obvious deletions | 5 |
| Cosmids oligolabeled and screened on Taq I and Msp I digested human DNAs | 43 |
| Cosmids with no detectable hybridization to human DNAs | 23 |
| Cosmids with repeats that obscured visualization of individual fragments | 2 |
| Cosmids revealing nonpolymorphic fragments | 10 |
| Cosmids revealing possible polymorphisms | 8 |

4. Preparation of Cosmid DNA

Figure 5A:
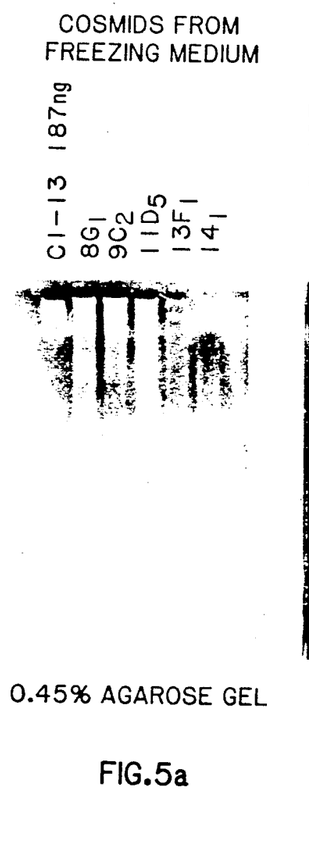
FIG. 5 shows cosmid DNA preparations wherein cosmid 1-13 served as a size standard and quantitative comparison.
Figure 5B:
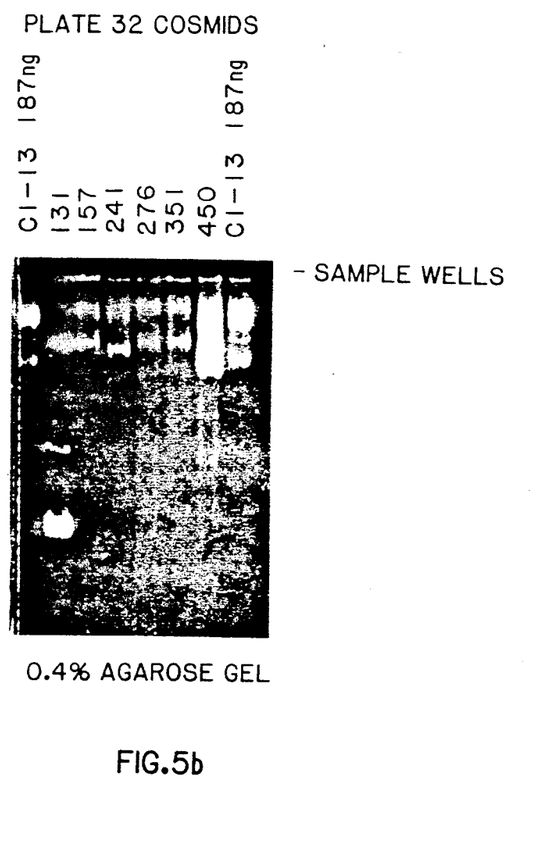

The next step was to prepare cosmid DNA from those clones that appeared to contain human inserts. Using the Birnboim alkaline miniprep method (Birnboim, Methods in Enzymology, 100:243-249, 1983), yields were consistently poor compared to those obtained with known plasmids and cosmids. Numerous modifications were tried with little improvement. FIG. 5a shows the results of a typical series of preparations from 4 ml of overnight culture of clones stored at −70 degrees C. in freezing medium as checked on a 0.45 percent agarose gel. A known control cosmid (not shown), 1-13, gave yields of about 1-2 µg per ml of fresh overnight culture while DNA from the test cosmids gave yields of 0-30 ng/ml. Lane 1 is 187 ng of cosmid 1-13 from a previous preparation to serve as a size standard and as a quantitative comparison. Preparations made from fresh overnight cultures from the −20 degrees C. gridded plates gave somewhat better, but still poor and highly variable, yields as shown in FIG. 5b. Yields ranged from unmeasurable to about 1 µg/ml of culture. Any measurable amount of DNA could not be obtained from 7 of the 50 cosmids.

During these initial minipreps, 5 of the 50 cosmids were found to be much smaller than 35-45 kb, having apparently deleted most of their DNA to less than 20 kb. They must have been larger initially as cosmids less than about 35 kb would not have packaged into bacteriophage λ (Old and Primrose, 1985). FIG. 5b shows one such deleted cosmid, CF32-131, in lane 2; FIG. 6 shows a second one, CF25-350, in lane 2.

In addition to the alkaline minipreps, large scale preparations including purification in cesium chloride (CsCl) gradients were attempted. Once again, poor or unmeasurable yields resulted. In fact, in most cases no cosmid DNA band was visible in the gradient after overnight ultracentrifugation. Only one intact cosmid, CF33-79, gave a measurable yield of 17.5 μg from 350 ml of culture. A good yield of 90 μg from 175 ml of culture containing cosmid CF33-176 was obtained, but it was subsequently discovered that the cosmid had deleted to several forms (FIG. 6), all less than 4 kb in size, indicating that they had lost part of the vector as well as the human insert. Another cosmid, CF 32-391, with a yield of 8μg of cosmid DNA from a 175 ml culture had deleted to about 6 kb.

5. Screening Cosmids for Polymorphisms

A total of 42 cosmids were labeled by nick translation, prehybridized with total human DNA, and screened on Southern blots containing Taq I and Msp I digested human DNAs from 6 to 9 unrelated individuals. Overall, 23 of the cosmids did not hybridize to any human DNA, i.e., the blots were blank except for the size standards. Two cosmids showed heavy lane background, 9 cosmids revealed nonpolymorphic fragments, and 8 cosmids revealed variable fragments that possibly represented polymorphisms. Six of the cosmids that did not hybridize to human DNA were later hybridized on Southern blots that included a lane of DNA from the somatic cell hybrid line used to make the library. In all cases, these probes hybridized strongly to the somatic cell hybrid DNA lane and not at all to the random human DNAs, indicating that these cosmids contained mouse inserts rather than human inserts. These 6 clones had initially been chosen as containing human inserts even though they had hybridized only very faintly with the total human DNA on colony screening because they did not appear to hybridize at all with the total mouse probe.

6. Further Screening of Cosmids Revealing Polymorphisms

Of the 8 cosmids that showed variable size fragments when hybridized to Taq I and Msp I digested total human DNAs, four showed enough variability to make additional screening worthwhile: CF32-391, CF32-435, CF33-79, and CF33-176. An autoradiograph from the initial screening of CF33-79 is shown in FIG. 7. CF32-435 showed a fragment pattern identical to that of CF 33-79 indicating that these 2 cosmids contained the same or an overlapping human insert.

CF32-391 revealed variable Taq I fragments of >18 kb and 6.6 kb. CF33-79 revealed variable Taq I fragments of 6.4, 3.7, 3.5, 3.1, and 2.9 kb (FIG. 7), and variable Msp fragments of 1.5 and 1.1 kb (Msp I blot not shown). CF33-176 revealed variable Taq I fragments at 7 kb and variable Msp fragments at 5.5 and 3 kb.

7. Cosmid CF33-79

The next step was to find single copy subclones of the cosmid that revealed specific polymorphisms. CF33-79 was studied first by cutting the cosmid with various 6-bp recognition sequence enzymes to find one that gave several well separated, moderate sized fragments so that these fragments could be recovered from LMT agarose and used as probes on Southern blots of Taq I, Msp I, and RsaI digested total human DNAs to find a single fragment that showed a polymorphism. At the same time, the cosmid was digested with Sau 3A and the fragments cloned into pSP65 to obtain about 200 subclones of the cosmid. The fragments revealing polymorphisms were used as probes of colony filters containing the subclones. Duplicate filters were also probed with total human DNA to eliminate subclones containing repetitive DNA. Subclones that hybridized to a fragment of interest but not to the total human DNA were chosen for further study by growing up the clones, isolating the plasmid DNAs, and using them as probes on the same or similar Southern blots as used above.

Figure 8:
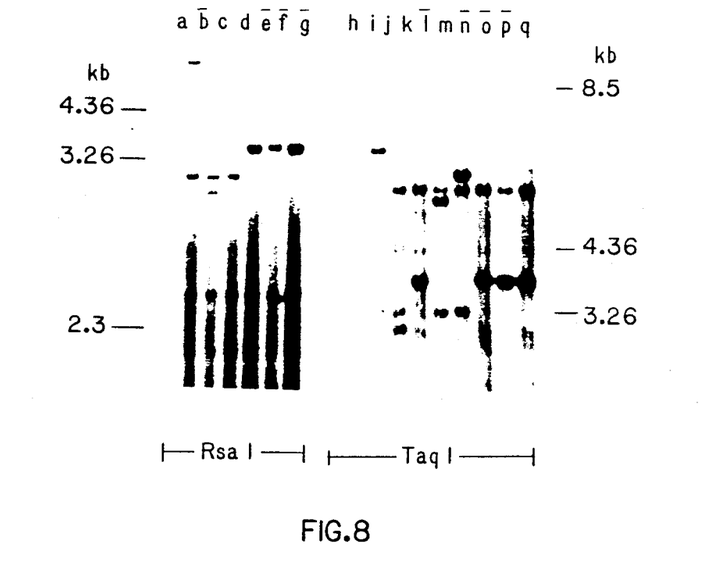
FIG. 8 is a photograph of Southern blots of RsaI and Taq I digested DNA from unrelated individuals probted with a 7.5 kb fragment of cosmid CF33-79.

CF33-79 was digested with Eco RI, Kpn I, Sac I, and Hind III. Eco RI gave the best size range with five well separated fragments of 25-30, 7.5, 5.8, 2.7, and 2.25 kb. When these fragments were oligolabeled, prehybridized with total human DNA, and used as probes on Southern blots, the 25 and 2.7 kb fragments hybridized to nonpolymorphic bands, the 2.25 kb fragment showed only faint lane background, and the 7.5 kb fragment revealed the Rsa I and Taq I polymorphisms shown in FIG. 8. The 5.8 kb fragment revealed the same Taq I polymorphism but hybridized only very weakly with the human DNA and very strongly with the size standards. This finding indicates that the 5.8 kb fragment includes the junction of the human insert and the vector.

Sau 3A fragments of CF33-79 were subcloned into the Bam HI site of pSP65, competent HB 101 were transformed with the ligation mix, and colonies containing recombinant plasmids were selected on ampicillin plates. From these plates, 2 master gridded plates containing about 100 colonies each were made. Replica filters from these plates were probed with oligolabeled total human DNA and with the oligolabeled 7.5 kb Eco RI cosmid fragment. Both hybridizations were done in duplicate. Thirteen subclones hybridized to the cosmid fragment but not to total human DNA. DNA preparations were made from these clones and from 6 others with inconclusive hybridization results. Of these 19 subclones, 5 had very small or no inserts and were not studied further. The remaining 14 subclones were hybridized with Southern blots as described above with the following results: 6 contained repeats so that single bands were not visible, 2 revealed nonpolymorphic bands, 3 produced blank or uninterpretable autoradiographs, and 3 (p79-1-98, p79-1-103, ∂ p79-2-23) showed the same polymorphisms revealed with the 7.5 kb cosmid fragment.

The Taq I and Rsa I polymorphisms appear to represent the same locus, that is, an insertion/deletion RFLP. The same locus was also observed when p79-1-103 was used on Southern blots of Hind III, Pvu II, Msp I, and Eco RI digested total human DNAs. This correlation between genotypes with 6 different enzymes is strong evidence for an insertion/deletion model. The equivalent size difference between allelic fragments found with Rsa I and Taq I, as shown in Table 2, is further evidence. The higher molecular weight allele sizes could only be estimated for Rsa I as 4.36 kb was the largest size standard on the blots whereas they were determined more accurately on Taq I blots which contained an 8.5 kb size standard.

TABLE 2

| CF33-79 RFLP* | | |
|---|---|---|
| Fragment Pattern (kb) | | Allele Frequency |
| Rsa I | Taq I | (102 chromosomes) |
| 7.1** | 7.3 | 0.01 |
| 6.2** | 6.4 | 0.08 |
| 5.9** | 6.1 | 0.13 |
| 5.1** | 5.3 | 0.02 |
| 4.8** | 5.0 | 0.03 |
| 4.5 | 4.7 | 0.01 |
| 3.9 | 4.1 | 0.05 |
| 3.5 | 3.7 | 0.19 |
| 3.3 | 3.5 | 0.04 |
| 3.0 | 3.2 | 0.37 |

TABLE 2-continued

| CF33-79 RFLP* | | |
|---|---|---|
| Fragment Pattern (kb) | | Allele Frequency |
| Rsa I | Taq I | (102 chromosomes) |
| 2.8 | 3.0 | 0.08 |

*This RFLP is seen with three subclones of CF33-79:p79-1-98, p79-1-103, and p79-2-23 with insert sizes of 1.45 kb, 3.0 kb, and 1.45 kb, respectively.
**Estimated size based on size of Taq 1 fragments.

FIG. 9, an autoradiograph of an Rsa I blot of 18 unrelated individuals probed with oligolabeled p79-2-23, shows the extensive variation at this locus among unrelated individuals. A total of 51 unrelated individuals were genotyped at this locus; 41 (80 percent) were heterozygous.

The RFLP was then studied in six 3-generation families, and Mendelian inheritance was observed in all cases. Lymphoblast cell lines from nine three-generation Utah families, each with all four grandparents and at least six children, were obtained from The Institute for Medical Research, Camden, N.J. Table 3 summarizes the parental genotypes in these families. FIG. 10 shows the co-dominant Mendelian inheritance of the RFLP in two families, K1331 and K1340.

TABLE 3

| CF33-79 RFLP | | |
|---|---|---|
| Parental Genotypes for Taq I fragments (kb) | | |
| Family | Father | Mother |
| K1329A | 3.2, 3.0 | 3.2, 3.2 |
| K1329B | 3.7, 3.2 | 6.1, 3.2 |
| K1329C | 3.2, 3.2 | 3.7, 3.0 |
| K1329D | 6.1, 3.2 | 3.2, 3.2 |
| K1331 | 6.1, 3.7 | 3.7, 3.5 |
| K1333 | 6.1, 6.1 | 6.4, 3.2 |
| K1340 | 3.7, 3.2 | 5.0, 3.2 |
| K1341 | 6.1, 3.2 | 5.0, 4.1 |
| K1345 | 3.2, 3.2 | 6.4, 3.2 |

C. Chromosomal localization of cosmid CF33-79

Chromosomal localization was done by two independent methods: use of a rodent x human somatic cell hybrid mapping panel and in situ hybridization. The hybrid cell panel and the methods used for in situ hybridization have been previously described (Buroker et al., Hum. Genet., 72:86–94, 1986; Litt et al., Hum. Genet., 73:340–345, 1986b). For in situ hybridization the entire nick-translated cosmid was used after prehybridization with total human DNA to remove repeated sequences.

The insert from p79-2-23 was used to probe a Southern blot containing Hind III-digested DNAs from 25 cell lines of a somatic cell-hybrid panel. As shown in FIG. 11 and Table 4, all 12 of the cell lines which contained chromosome 16 hybridized with the probe; all other chromosomes had at least five discordancies. In FIG. 11, E26 and RAG are the hamster and mouse parents, the lane marked ss contains the size standards, and the sizes of human-specific Hind III fragments which hybridize to the probe are shown on the left.

TABLE 4

Chromosome contents of hybrid cell lines. The designations are: +, presence or −, absence of a human chromosome: R, rearranged chromosome as determined by disruption of a syntenic group or by a cytogenetic abnormality, ±, chromosome present in less than 15 per cent of cells and/or the isozyme or DNA probe characteristic of the chromosome weakly positive; p, presence of a marker for the short arm and absence of a marker for the long arm; q, presence of a marker for the long arm and absence of a marker for the short arm; a, Xq24→qter; ND, not done. For calculation of the discordancy fractions, hybrids with a rearranged chromosome or those where the chromosome was present in less than 15 per cent of the cells were excluded from analysis. The column designated M indicates the presence or absence of human-specific Taq I fragments in Southern transfer probed with p79-2-23.

| Cell line | Chromosome complement | | | | | | | | | | | | | | | | | | | | | | | | Scoring M |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y | |
| G35D5 | + | + | + | − | − | + | + | − | − | + | − | − | + | + | + | ± | + | + | + | + | − | + | a | − | − |
| G35F3 | − | + | + | − | + | − | + | + | − | + | + | + | − | − | − | + | − | + | + | + | − | − | a | − | + |
| G35D2 | ± | − | − | − | + | + | − | − | + | − | + | + | − | − | + | − | − | + | R | + | − | + | aR | − | − |
| G35E3 | − | − | − | − | + | + | − | + | − | − | + | + | + | + | − | + | − | + | + | + | + | + | a | − | + |
| G35A2 | − | − | + | ± | − | + | − | − | − | − | − | + | − | + | − | − | − | − | + | + | + | + | − | − | − |
| G35C2 | − | − | − | + | − | − | − | + | − | − | R | − | − | + | − | + | − | − | R | − | − | − | R | − | + |
| G35C4 | − | − | − | − | − | + | − | − | R | − | − | + | − | + | − | − | − | ± | + | + | + | − | a | − | − |
| G35B5 | − | − | − | − | − | R | + | − | − | − | + | p | + | − | − | − | + | − | + | + | − | − | a | − | − |
| G35F5 | ± | − | + | + | − | + | − | − | + | − | + | − | + | + | − | + | + | + | + | ± | + | + | + | − | + |
| G35D3 | − | p | − | ± | − | − | + | + | + | + | − | − | − | ± | − | ± | + | − | + | + | + | + | a | − | + |
| G35C5 | − | − | p | − | + | − | + | + | + | + | − | p | − | − | + | + | + | − | + | + | + | + | a | − | + |
| G35A4 | + | − | + | + | − | + | − | + | + | − | − | − | − | + | − | + | − | − | + | + | + | − | a | − | + |
| G35B4 | + | − | − | − | + | − | − | − | − | + | + | + | − | − | − | − | − | + | + | − | − | + | + | − | − |
| G35E4 | − | − | − | R | − | − | − | − | R | − | − | − | − | − | + | − | − | − | + | − | − | − | a | − | − |
| G175 | ± | − | − | + | − | + | − | + | − | + | − | − | + | + | + | − | − | − | + | − | − | + | a | − | − |
| G24A9 | − | + | − | + | − | + | − | + | + | + | − | − | ± | + | + | − | ± | + | + | − | + | − | q | − | − |
| G24A4 | ± | p | − | − | + | + | + | − | ± | − | ± | − | + | + | + | + | − | − | + | − | + | − | q | − | + |
| G24B5 | + | − | + | + | − | − | + | − | − | + | + | + | + | + | − | + | − | − | + | − | + | + | + | − | + |
| G89E5[a] | − | − | − | − | − | − | − | − | − | − | − | − | − | − | − | − | − | − | − | − | − | − | + | − | − |
| G95A4 | − | − | − | − | − | − | − | − | − | − | − | − | − | − | − | − | − | − | − | ± | − | − | + | − | − |
| G35A5AzA[b] | | | | | | | | | | | | | | | | + | | | | | | | | | + |
| G35A5AzF[b] | | | | | | | | | | | | | | | | ± | | | | | | | | | + |
| RRP5-7 | + | − | − | + | + | − | + | − | − | + | − | + | ND | + | − | + | + | − | + | − | − | + | R | | + |
| RRP3-6B1 | + | + | + | + | + | + | + | − | − | + | + | − | − | − | + | + | R | − | + | − | + | + | | | + |
| G35F1 | − | − | − | + | + | − | − | + | − | ± | − | p | − | + | − | − | + | + | + | − | a | − | − | | |
| Discordancy | 8 | 7 | 5 | 8 | 8 | 10 | 9 | 8 | 8 | 11 | 6 | 9 | 9 | 9 | 11 | 0 | 10 | 12 | 10 | 7 | 10 | 11 | 5 | 8 | |

TABLE 4-continued

Chromosome contents of hybrid cell lines. The designations are: +, presence or −, absence of a human chromosome: R, rearranged chromosome as determined by disruption of a syntenic group or by a cytogenetic abnormality, ±, chromosome present in less than 15 per cent of cells and/or the isozyme or DNA probe characteristic of the chromosome weakly positive; p, presence of a marker for the short arm and absence of a marker for the long arm; q, presence of a marker for the long arm and absence of a marker for the short arm; a, Xq24→qter; ND, not done. For calculation of the discordancy fractions, hybrids with a rearranged chromosome or those where the chromosome was present in less than 15 per cent of the cells were excluded from analysis. The column designated M indicates the presence or absence of human-specific Taq I fragments in Southern transfer probed with p79-2-23.

| Cell line | Chromosome complement | | | | | | | | | | | | | | | | | | | | | | | | Scoring M |
|---|---|---|---|---|---|---|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |  |
| Fraction | 19 | 21 | 22 | 20 | 23 | 22 | 23 | 23 | 20 | 22 | 21 | 20 | 21 | 22 | 23 | 24 | 22 | 22 | 20 | 21 | 23 | 23 | 8 | 22 |  |

[a] Cell line G89E5 contains an X chromosome in all cells plus an unidentified human-hamster translocation in about 20 percent of the cells.
[b] Cell lines G35A5AzA and G35A5AzF are subclones of G35A5 detected in 8-azaguanine for loss of the der(19) translocation chromosome t(X:19)q23-25::q13 (Latt et al. 1976). Although these cell lines have not been extensively characterized, they both hybridized to a probe for haptoglobin, known to reside on chromosome 16q22.1 (Willard et al. 1985).

More precise localization was obtained by in situ hybridization of cosmid CF33-79. A representative, sequentially stained metaphase spread from the in situ hybridization study is shown in FIG. 12. In FIG. 12a, the representative metaphase has been R-banded following hybridization. In FIG. 12b, the same metaphase has been destained and restained with Wright's stain to show silver grains. The arrow in each panel indicates the silver grain, located over the tip of chromosome 16q and the corresponding location in the R-banded metaphase. The silver grains revealing hybridization of the probe are observed with standard stain while the identification of the chromosomes to which the probe has annealed is by their fluorescent R-banding pattern.

FIG. 13 summarizes the results of scoring 110 labelled metaphase spreads from a normal male. Twenty-four of the 110 metaphases (22 percent) showed hybridization to the distal portion of 16q, (16q22→q24); the rest of the label was randomly distributed over the chromosomes. Similar results were obtained when the single-copy subclone p79-2-23 was used as a probe for in situ hybridization (data not shown).

The name D16S7 has been assigned to the locus which maps to 16q22→q24, has at least 11 alleles, and has a PIC of 0.77. Subclone p79-2-23 detects this locus.

D. Substantially Homologous Probes

The present invention includes DNA probes which contain a sequence substantially homologous or substantially identical to at least a portion of the base pair sequence of probe p79-2-23. A substantially homologous sequence is one in which a high degree of homology between the sequences of two or more DNA molecules can be tested for by determining whether the DNA molecules in question hybridize to each other under stringent conditions, such as those set forth in Bethesda Research Laboratories, DNA Detection System Instruction Manual (Catalogue No. 8239SA), pp. 8-9 (1984). See also Leary et al., Proc. Natl. Acad. Sci. USA, 80:4045-4049 (1983), modifying the procedures of Wahl, et al., Proc. Natl. Acad. Sci. USA, 76:3683-3687 (1979).

E. Probe Uses

The DNA fingerprints produced by probe p79-2-23 are sufficiently stable and individual-specific for use in human identification in, for example, forensic medicine. Badly disfigured corpses can be identified by preparing a genetic fingerprint with probe p79-2-23, and comparing the fingerprint to bands produced by DNA of a previously collected tissue sample from a known individual who is believed to be the corpse. If the band patterns match, identity has probably been established. Rapists can similarly be identified by comparing the band patterns from semen in the victim with the band patterns produced by the DNA of an individual suspected of committing the crime.

The simple Mendelian inheritance of band patterns produced by p79-2-23 makes it possible to use the probe in determining parentage, for example, in a disputed paternity suit. Approximately half of the polymorphic fragments in an offspring are derived from the father, and these paternal fragments can be identified by comparison of the mother's and offspring's DNA band patterns. All fragments present in the offspring but not in the mother must be present in the father (allowing for a possible rare new mutation). The large number of polymorphic fragments makes it possible not only to exclude paternity, if bands are present in the offspring but not the mother or putative father, but also to predict statistically the possibility of inclusion of paternity.

Probe p79-2-23 is a potentially useful tool for following engraftment of donor bone marrow after transplanation (Blazar, et al., Blood, 66:1436-1444 (1985)), and for many forensic applications. Furthermore, p79-2-23 might be useful in isolating genomic clones capable of revealing additional hypervariable regions.

RFLPs are also useful in cancer research to determine clonal origin of tumors and to study the loss of heterozygosity at various gene loci. Vogelstein, et al., Science, 227:642-644 (1985); Dracopoli, et al., Proc. Natl. Acad. Sci. USA, 82:1470-1474 (1985). Restriction Enzyme Mapping Probe p79-2-23 can also be used to map genes on chromosomes using the techniques disclosed by Gusella, et al. (1983), Murray, et al. (1982), Bhattacharya, et al. (1984), Reeders, et al. (1985) or Tsui, et al. (1985). A disease gene can be located by using the knowledge that a RFLP closely linked to a gene would be inherited with that gene. The inheritance of numerous RFLPs in families having the disease can be traced using random cloned DNA fragments from a human gene library as probes. An RFLP which is found to be inherited along with the disease indicates that the RFLP and disease gene are closely linked. Probe p79-2-23 will therefore indicate the presence of a disease gene on the long arm of human chromosome 16.

ATCC Deposit

Probe p79-2-23 has been deposited with American Type Culture Collection in Rockville, Md., and assigned ATCC accession No. 40327. The deposited probe is a plasmid containing an insert DNA from cosmid CF33-79. In use, the probe would be amplified through bacterial transformation to produce a bacterial colony. The plasmid would then be isolated and labeled, for example, with radioactive phosphorous.

Having illustrated and described the principles of the invention in a preferred embodiment, it should be apparent to those skilled in the art that the invention can be modified in arrangement and detail without departing from such principles. We claim all modifications coming within the spirit and scope of the following claims.

We claim:

1. A plasmid having ATCC accession No. 40327, which plasmid is a clone of DNA probe p79-2-23.

2. A DNA probe containing a sequence of the inserted DNA of a plasmid having ATCC accession No. 40327, which insert hybridizes to chromosome b 16 of the human genome.

3. The probe of claim 2 further comprising a label which enables detection of the probe.

4. The probe of claim 2 that is a plasmid.

5. A recombinant DNA molecule comprising:

A DNA segment containing a sequence from a portion of the inserted sequence of probe p-79.2.23, the sequence being capable of hybridizing to chromosome 16 of the human genome in such a manner that the molecule can be used to detect a restriction fragment length polymorphism in humans, the sequence including a sufficient number of bases that, when the molecule is hybridized to polymorphic fragments which are obtained by digesting the D16S7 locus of a human subject's genome and which are separated by Southern blotting, the resulting blot has a distinctive band pattern that is characteristic of the subject from which the genome was taken; and a label for detecting the molecule.

6. The molecule of claim 5 that is a plasmid.

7. The probe of claim 3 wherein the label is a radioactive material.

8. The probe of claim 7 wherein the radioactive material is phosphorous.

9. The probe of claim 5 wherein the label is a radioactive material.

10. A DNA probe containing the DNA sequence of p-79-2-23, the sequence being capable of hybridizing to chromosome 16 of the human genome in such a manner that the probe can be used to detect a restriction fragment length polymorphism in humans, the sequence including a sufficient number of bases that, when the probe is hybridized to polymorphic fragments which are obtained by digesting the D16S7 locus of a human subject's genome and which are separated by Southern blotting, the resulting blot has a distinctive band pattern that is characteristic of the subject from which the genome was taken.

11. A DNA probe having a nucleotide sequence which hybridizes to at least a portion of locus D16S7 of chromosome 16 in the human genome in such a manner that the probe can be used to detect a restriction fragment length polymorphism in humans, and which reveals at least 11 fragments varying in size from 3.0 to 7.3 kb when used to probe Taq I digested DNA from the D16S7 locus, the sequence including a sufficient number of bases that, when the probe is hybridized to polymorphic fragments which are obtained by digesting the Db 16S7 locus of a human subject's genome and which are separated by Southern blotting, the resulting blot has a distinctive band pattern that is characteristic of the subject from which the genome was taken.

12. A DNA probe which hybridizes to a hypervariable region of the human genome at locus D16S7 and reveals a multiple allele RFLP with at least eleven fragments varying in size from 3.0 to 7.3 when used to probe Southern blots of TaqI-digested DNA.

* * * * *